United States Patent [19]

Cuzzato et al.

[11] Patent Number: 5,981,813
[45] Date of Patent: Nov. 9, 1999

[54] FLUORINATION PROCESS OF HALOGENATED ORGANIC COMPOUNDS

[75] Inventors: Paolo Cuzzato, Treviso; Letanzio Bragante; Francesco Rinaldi, both of Padua, all of Italy

[73] Assignee: Ausimont S.p.A., Milan, Italy

[21] Appl. No.: 09/081,296

[22] Filed: May 20, 1997

[30] Foreign Application Priority Data

May 22, 1996 [IT] Italy ................................. MI97A1194

[51] Int. Cl.⁶ .................................................. C07C 17/08
[52] U.S. Cl. .......................... 570/166; 570/169; 502/228
[58] Field of Search ..................... 570/169, 166

[56] References Cited

U.S. PATENT DOCUMENTS

| | | | |
|---|---|---|---|
| 3,697,443 | 10/1972 | Shinoda et al. | 570/166 |
| 4,967,023 | 10/1990 | Carmello et al. | |
| 5,008,475 | 4/1991 | Manzer et al. | |
| 5,300,711 | 4/1994 | Corbin et al. | |
| 5,545,778 | 8/1996 | Tung et al. | |

FOREIGN PATENT DOCUMENTS

| | | | |
|---|---|---|---|
| 0 282 005 | 9/1988 | European Pat. Off. | |
| 0 408 004 A1 | 1/1991 | European Pat. Off. | |
| 0 408 005 A1 | 1/1991 | European Pat. Off. | |
| 0 408 005 B1 | 1/1991 | European Pat. Off. | |
| 514932 | 11/1992 | European Pat. Off. | 570/169 |
| 0 537 760 A2 | 4/1993 | European Pat. Off. | |
| 0 609 123 A1 | 8/1994 | European Pat. Off. | |
| 0 687 660 A1 | 12/1995 | European Pat. Off. | |
| 1 266 439 | 3/1972 | United Kingdom. | |
| WO 90/08755 | 8/1990 | WIPO. | |

*Primary Examiner*—Alan Siegel
*Attorney, Agent, or Firm*—Nikaido Marmelstein Murray & Oram LLP

[57] ABSTRACT

Fluorination process of halogenated organic compounds with gaseous anhydrous HF characterized in that a catalyst comprising a supported Cr(III) amorphous compound is used, wherein the support consists in an aluminum trifluoride ($AlF_3$) having an high surface area and an high pore volume obtainable by fluorination with gaseous HF of alumina having surface area of at least 150 $m^2/g$ and pore volume not lower than 0.3 cc/g and wherein said alumina comprises from 0.5 up to 15% by weight of silicon oxide, the chromium amount being comprised between 1 and 20% by weight.

3 Claims, No Drawings

FLUORINATION PROCESS OF HALOGENATED ORGANIC COMPOUNDS

The present invention relates to the preparation of an improved catalyst for the fluorination of halogenated organic compounds with gaseous anhydrous HF.

More specifically, the present invention relates to a catalyst for the synthesis of hydrohalocompounds H(C)FC of the 120 and 130 series. In particular those of the 120 series have the general formula $C_2HX_5$ (monohydropentahaloethanes) wherein X can indifferently be fluorine or chlorine, provided that there is at least a fluorine atom. These compounds are commercially known as HFC/HCFC "120 series".

In particular for the 130 series the general formula is $CF_3CH_2X$ wherein X has the above meaning. These products are commercially well known as products of the 130 series, specifically 134a wherein x=F.

For the synthesis of the 120 series compounds one refers in particular to the PCE (perchloroethylene) fluorination with gaseous anhydrous HF, on catalyst in heterogeneous phase.

For the 130 series the invention preferably refers to the trichloroethylene fluorination with HF to obtain $CF_3$—$CH_2Cl$ (HCFC-133a), and subsequent fluorination of $CF_3$—$CH_2Cl$ (HCFC-133a) to obtain $CF_3$—$CH_2F$ (HFC-134a).

It is well known the industrial utility to have available efficient catalysts for the above reactions, by which, for instance, HCFC 123, 124 and 133a and HFC 125 and 134a, not dangerous for the ozone layer, are produced, which replace the chlorofluorocarbons (CFC) banned by the Montreal protocol: see for instance U.S. Pat. No. 4,967,023, U.S. Pat. No. 5,008,475, EP 408,005, WO 90/08755.

Most of these processes use a catalyst in heterogeneous phase formed by a trivalent chromium compound, sometimes supported on a suitable support such as alumina, aluminum fluoride or carbon.

In particular for the 120 series the three compounds mentioned before are generally produced starting from perchloroethylene either by processes in a single step—wherein in a single reactor a mixture of the three compounds is obtained—or in more steps, by isolating $CHCl_2$—$CF_3$ (HCFC-123) and/or $CHClF$—$CF_3$ (HCFC-124) and feeding them to a second reactor for the production of HCFC-124 and/or $CHF_2$—$CF_3$ (HCFC-125). Of course the single step processes are simpler and cheaper than the two or more steps, since they require a lower investment for the plant.

However the single step processes, that is, those starting from perchloroethylene (PCE) and directly bringing to the products, of the art, mainly lead to the formation of HCFC-123 and 124, with small production of HFC-125. The production of HFC-125 can be increased only by using particularly extreme reaction conditions (high temperatures, large excess of HF or long contact times) which are not favourable in industrial scale, since they lead to unacceptably decrease, respectively, the selectivity or the productivity of the process. See in particular U.S. Pat. No. 5,545,778, wherein even though relatively high temperatures and pressures (330° C. and 50 psig) and a large excess of HF (molar ratio HF/PCE=8/1), are used, an yield in HFC-125 of only 10% is obtained (as yield it is meant, in the present invention, the ratio between produced 125 and converted PCE). Similarly in U.S. Pat. No. 5,300,711 and U.S. Pat. No. 5,008,475 the yield in HFC-125 ranges from 0.4 to 11% depending on the catalysts and the reaction conditions, with very low selectivity in some cases.

One is thus obliged, to produce valuable amounts of HFC-125, to recycle to the reactors large amounts of HCFC-123 and/or 124 obtained in the process, with evident charge of the recycles (reaction loop), increases of the energetic costs and proportional reduction of the amount of fresch PCE fed to the reactor. Alternatively one can resort to a two step process, wherein HCFC-123 and/or 124 produced in a first reactor are fed to a second reactor, which works under more severe conditions than the first, as for instance in EP 0687,660. Such process has the drawback that not only two reactors are needed, but it uses more severe reaction conditions in the second reactor which lower the process selectivity and allow the formation of remarkable amounts of CFC-115 (up to 15% with respect to 125 as shown in the above mentioned EP 687,660).

The CFC-115 is an highly undesirable contaminant which must be removed from the products by means of suitable treatments.

Moreover, by using said drastic conditions in the second reactor the decay of the catalyst is accelerated, which must be regenerated at intervals, generally by coke combustion deposited thereon, with hot air: what results very expensive for the need to stop the plant with consequent non-production.

In order to overcome the need to stop the plant it has been suggested (see U.S. Pat. No. 5,545,778) to add small amounts of an oxidizing agent (air or oxygen) to the reaction mixture itself, so that the contaminants are burnt as they are formed. This however, on one hand, is potentially dangerous for the known instability of the halogenated epoxides which could be formed in the reaction mixture, on the other, it further lowers the process selectivity since, in the presence of the HCl produced by the reaction, the well known oxychlorination reaction occurs, thus producing CFCs of no utility:

Similar problems, in particular of catalyst decay, occur also in the process for obtaining the 130 series.

The need is therefore felt to have a process in a single step for the production of the above compounds, without the above problems: in particular the need is felt of a catalyst capable to promote the PCE hydrofluorination to compounds "120 series", having high activity, long life and capable to givie the desired mixture of products in a single reaction step.

It has been unexpectedly and surprisingly found a catalyst as defined hereinafter, its preparation process and a process for the fluorination of halogenated organic compounds with gaseous anhydrous HF which is capable to operate for a long time with high selectivity and conversion, overcoming the above problems.

It is an object of the present invention a catalyst comprising a supported Cr(III) amorphous compound, characterized in that the support consists in an aluminum trifluoride ($AlF_3$) having an high surface area and an high pore volume obtainable by fluorination with gaseous HF of alumina having surface area of at least 150 m$^2$/g and pores volume not lower than 0.3 cc/g and wherein said alumina comprises from 0.5 up to 15% by weight of silicon oxide, preferably from 1 to 10% by weight, more preferably from 1.5 to 6% by weight. The chromium amount is comprised between 1 and 20% by weight, preferably 5 and 15% by weight.

The catalyst preparation can be carried out with methods known in the art, among which the Applicant has found particularly suitable the one defined in the art by "incipient wetness", described hereinafter. However any other suitable method can of course be used, as known to the skilled in the art of the catalyst preparation.

The catalyst preparation general preferred procedure according to the above method consists in impregnating a determined amount of support obtained with the above method with a concentrated solution of a soluble Cr(III) salt, for instance chloride. The volume of the impregnating solution is equal to or lower than the volume of the support pores, in order to avoid the adhesion among the grains of the same.

Then a first drying treatment is carried out at a moderate temperature—for instance 120° C.—to evaporate water and to allow salt deposition. If necessary, this procedure is repeated many times until the desired amount of metals on the support is reached.

After the last drying the catalyst is transferred to a tubular reactor and calcined for some hours at 300°–400° C. under inert gas flow, for instance, nitrogen. The final activation is then carried out with a fluorinating agent: generally an anhydrous HF flow is fed to the same reactor and the nitrogen flow is reduced little by little until the desired HF concentration, which can also be pure HF. Alternatively the catalyst can be transferred to the fluorination reactor and activated in situ with the same mixture of the reactants (HF+organic reactants).

A further object of the present invention is a fluorination process of halogenated organic compounds with gaseous anhydrous HF characterized in that the chromium catalyst supported as defined above is used.

In particular the fluorination process relates to the PCE fluorination to 120 series, specifically to obtain compounds having the general formula $C_2HX_5$ wherein x is equal to F, Cl or to produce trichloroethylene (TCE) to obtain the products of the 130 series having the general formula $CF_3CH_2X$ wherein X has the above meaning.

In order to obtain the most fluorinated products, instead of starting from PCE or TCE, one can use the lower fluorinated products having respectively the above formulas.

In the fluorination processes of halogenated organic compounds the catalysts of the present invention show high selectivity, efficiency and duration, and make possible, for instance for the 120 series, to vary in a wide range the relative amounts of the obtained fluorinated products.

In the fluorination, atmospheric or superatmospheric pressure, preferably the superatmospheric up to 15 atm, can be used.

As aluminum trifluoride, used as support, according to the present invention, it is meant the alumina fluorination product, with a fluorine content not lower than 90%, preferably not lower than 95%, of the stoichiometric.

The catalyst of the invention, as already said, keeps an high activity during the time wherefore it does not require frequent regeneration processes.

The $AlF_3$ support obtainable with the above process generally has a surface area not lower than 25 $m^2/g$, preferably not lower than 30 $m^2/g$ and a pore volume not lower than 0.20 cc/g, preferably 0.25 cc/g.

Fluorination conditions of alumina containing silica are not particularly critical, one generally operates at a temperature between about 250° C. and about 450° C., preferably higher than 300°–400° C.

It is on the contrary advantageous that the HF partial pressure is low, especially at the beginning of the fluorination, to moderate the heat development which could locally increase the temperature over the before mentioned limits: indeed two highly exothermal phenomena contemporaneously occur: the reaction between HF and alumina with formation of $AlF_3$ and water and the hydration of the unreacted HF by the latter.

To moderate this exothermy it is sufficient to use HF diluted with a gas inert under the fluorination conditions, for instance, air or nitrogen; the HF partial pressure is generally comprised between 0.1 and 0.50.

The aluminas used in the preparation of the support and containing silica are prepared with methods known in the art, for instance by spray-drying of suitable precursors: commercial products, for instance those of Condea Chemie GmbH of Hamburg, Germany, can be used.

Said support $AlF_3$ obtained with the mentioned process is generally mainly formed by gamma phase as described in FR 1,383,927.

Some examples for preparing the particular support, the catalyst and of its use in fluorination ractions are given hereinafter.

EXAMPLE 1

Preparation of $AlF_3$ by Using an Alumina CONDEA SIRAL® 1.5 Containing 1.5% of Silica An alumina containing 1.5% of silica (% by weight of the anhydrous product) is calcined under air flow at 360° C. After calcination it results to have:

SA=305 $m^2/g$

Vp=0.442 $cm^3/g$

DRX: pseudo-bohemite.

370 g of this alumina are introduced in an Inconel 600® tubular reactor having a 50 mm diameter, electrically heated and equipped with porous septum at the base, and fluorinated with an air/HF mixture at the temperature of 360° C. for 30 hours; at steady conditions the mixture composition is:

0.85 mole/hours of HF, 4 mole of air.

The flow air is allowed to cool: about 510 g of $AlF_3$ are obtained with the following characteristics:

SA=34.5 $m^2/g$

Vp=0.26 $cm^3/g$ crystalline structure: $\gamma$-$AlF_3$ with a little of $\alpha$-$AlF_3$.

EXAMPLE 2

Preparation of $AlF_3$ from an Alumina SIRAL® 5 Containing 5.4% of Silica

The CONDEA SIRAL® 5 alumina is calcined as described in Example 1. After calcination it results to have:

SA=295 $m^2/g$

Vp=0.499 $cm^3/g$

DRX: pseudo-bohemite.

370 g of this alumina are fluorinated as described in the preceding example: about 530 g of $AlF_3$ are obtained having the following characteristics:

SA=43.0 $m^2/g$

Vp=0.35 $cm^3/g$ crystalline structure: $\gamma$-$AlF_3$ with a little of $\alpha$- and $\beta$-$AlF_3$.

EXAMPLE 3

Preparation of a Catalyst According to the Invention 500 g of $AlF_3$ obtained in Example 1, starting from an alumina containing 1.5% by weight of silica, are impregnated with 295 cc of a solution prepared by dissolving 324 g of $CrCl_3.6H_2O$ in the necessary water volume.

The so impregnated catalyst is treated in fluidized bed with 100 l/h of nitrogen at 400° C. for 10 hours, then with 100 g/h of anhydrous HF at 360° C. for 24 hours, as above described. A catalyst is thus obtained containing about 10.5% by weight of chromium (AAS analysis).

EXAMPLE 4
PCE Fluorination at 280° C.

248 g (220 cc) of the catalyst prepared in Example 3 are placed in an Inconel 600 tubular reactor having a 50 mm diameter, and heated to 280° C. under nitrogen flow. At this temperature the nitrogen is replaced by anhydrous HF 858 g/h. To the HF 96 g/h of PCE are then added, thus achieving a contact time of 5 sec. and an HF/PCE ratio of 5/1; the contact time is meant as the ratio between the reactant volume at the reaction temperature and the apparent volume of the non fluidized catalyst bed.

The gases flowing out from the reactor are washed to remove the acidity and analysed by GLC. The following analysis is representative of the obtained results:

| HFC-125 | 5.2% molar |
|---|---|
| HCFC-124 (2 isomers) | 12.5 |
| HCFC-123 (3 isomers) | 23.2 |
| recyclable intermediates (HCFC-121, 122, 1111) | 5.8 |
| non recyclable by-products (CFC-113, 114 and HCFC-133a, etc.) | 0.6 |
| PCE | 52.7. |

The PCE conversion results to be 47.3%, the selectivity in 120 series products is equal to 0.99, the by-products are equal to 1.3% of the converted PCE.

The run is carried on for 65 hours, during which the conversion remains constant at 47–48% and the selectivity is constant at 98–99%.

EXAMPLE 5
PCE Fluorination at 300° C.

With the same catalyst of Example 4 which has already worked for 65 hours at 280° C., the reaction temperature is brought to 300° C., all the other conditions remaining unchanged (the flows are regulated in order to keep constant the contact time with the temperature increase: HF 56 g/h and PCE 93 g/h). The conversion rises up to 55–56% and the selectivity is of about 98%; after further 70 hours (135 total hours) the conversion has a very poor decay, by decreasing to about 53% (95% of the initial activity). The following analysis is representative of the results obtained at 300° C.:

| HFC-125 | 16.9% molar |
|---|---|
| HCFC-124 (2 isomers) | 13.8 |
| HCFC-123 (3 isomers) | 19.0 |
| recyclable intermediates (HCFC-121, 122, 1111) | 4.3 |
| non recyclable by-products (CFC-113, 114 and HCFC-133a, etc.) | 1.1 |
| PCE | 44.9. |

The PCE conversion is 55.1% and the by-products represent 2.1% of the converted product.

As it can be seen from the comparison between Examples 4 and 5, it is possible to obtain variable amounts of HFC-125 by slightly modifying the reaction temperature, with a quite insignificant effect on the selectivity.

EXAMPLE 6
(Comparative)

A catalyst similar to that of Example 3 is prepared, by using an $AlF_3$ support prepared by starting from an alumina free from silica (commercial product CONDEA PURAL®-SCC10) which after calcination under air flow at 360° C. results to have:

SA=275 m$^2$/g

Vp=0.402 cc/g crystalline structure: pseudo-bohemite 370 g of this alumina are fluorinated as described in Example 1. About 510 g of aluminum fluoride are obtained, having the following characteristics:

SA=19.8 m$^2$/g

Vp=0.19 cc/g crystalline structure: gamma-$AlF_3$ 500 g of the so obtained aluminum fluoride are impregnated with 225 cc of aqueous solution containing 248 g of $CrCl_3.6H_2O$.

The so obtained catalyst is activated with nitrogen and then with anhydrous HF as described in Example 3.

300 cc (379 g) of activated catalyst are placed in the same reactor of the preceding Examples. At the temperature of 280° C., 131.5 g/h of PCE and 79 g/h of anhydrous HF are fed, thus achieving a contact time of 5 sec. and a molar ratio HF/PCE equal to 5.

The following analysis is representative of the obtained results:

| HFC-125: | 1.5% moles |
|---|---|
| HCFC-124 | 6.4 |
| HCFC-123 | 12.0 |
| intermediates | 5.0 |
| by-products | 0.8 |
| PCE | 73.3. |

The PCE conversion is 26.7% and the by-products are 3.0% of the converted product. As it can be seen, the catalyst activity is much lower than that of the invention, both in terms of global conversion and of productivity in HFC-125, even without a corresponding gain on the selectivity. Also the catalyst decay is quicker than in the preceding Examples, it decreases to 90% of the initial activity in 56 hours.

EXAMPLE 7A
Preparation of 134a (130 series) Starting from 133a

A catalyst is prepared starting from a support of $AlF_3$ prepared as in Example 2.

400 g of $AlF_3$ of Example 2 are impregnated with 369 cc of a solution containing 406 g of $CrCl_3.6H_2O$ and activated as described in Example 3.

200 g of activated catalyst are placed in a reactor having the same characteristics as that of the preceding Examples.

At the temperature of 320° C. a mixture of HCFC-133a and HF is fed such as to achieve a molar ratio HF/HCFC-133a=4 and a contact time of 2.5 sec.

The following analysis is representative of the obtained products expressed in % by mole:

| HFC-134a | 14.5 |
|---|---|
| HCFC-133a | 85.3 |
| others | 0.17 |

The 133a conversion remains equal to or higher than 14% for about 170 hours of running. The selectivity in HFC-134a is ≧99%

EXAMPLE 7B

The fluorination after 170 hours of running of Example 7a is continued under the same conditions but bringing the temperature to 360° C.

The HCFC-133a conversion rises up to 21% and remains constant for further 75 hours of running. The selectivity in HFC-134a is of 98–99%.

EXAMPLE 7C

The fluorination of Example 7B is carried on with the same catalyst which has worked for 245 total hours, maintaining the same conditions but bringing the temperature to 380° C.

The HCFC-133a conversion rises up to 22.5–23% and the selectivity is 98.5%.

At this temperature a certain decay of the catalyst starts which brings the conversion to 20–20.5% about after further 50 hours, for a total of 300 hours of running, during which over 40 kg of 133a, equal to over 200 times the catalyst weight, were fed.

We claim:

1. A process for fluorinating halogenated organic compounds with gaseous anhydrous HF, said process including contacting reactants with a supported Cr(III) amorphous compound, characterized in that the support consists of an aluminum trifluoride ($AlF_3$) having a high surface area and a high pore volume obtained by fluorinating alumina having a surface area of at least 150 $m^2/g$ and pore volume not less than 0.3 cc/q with gaseous HF, said alumina comprises from 0.5 up to 15% by weight of silicon oxide, and the chromium content thereof is between 1 and 20% by weight.

2. The process according to claim 1, wherein the halogenated organic compound is perchloroethylene (PCE) so that products of the 120 series are obtained having the general formula $C_2HX_5$ wherein X is equal to F or Cl.

3. The process according to claim 1 wherein the halogenated organic compound is trichloroethylene (TCE) so that products of the 120 series are obtained having the general formula $CF_3CH_2X$ wherein X is equal to F or Cl.

* * * * *